United States Patent
Yeh et al.

(10) Patent No.: US 11,839,748 B2
(45) Date of Patent: Dec. 12, 2023

(54) PLUNGING APPARATUS FOR SYRINGE

(71) Applicant: CC Biotechnology Corporation, Tainan (TW)

(72) Inventors: Chin-Min Yeh, Tainan (TW); Satyashodhan Patil, Vadodara (IN)

(73) Assignee: CC BIOTECHNOLOGY CORPORATION, Tainan (TW)

( * ) Notice: Subject to any disclaimer, the term of this patent is extended or adjusted under 35 U.S.C. 154(b) by 500 days.

(21) Appl. No.: 16/965,999

(22) PCT Filed: Sep. 7, 2018

(86) PCT No.: PCT/CN2018/104607
§ 371 (c)(1),
(2) Date: Jul. 29, 2020

(87) PCT Pub. No.: WO2020/047841
PCT Pub. Date: Mar. 12, 2020

(65) Prior Publication Data
US 2021/0369967 A1  Dec. 2, 2021

(51) Int. Cl.
*A61M 5/315* (2006.01)

(52) U.S. Cl.
CPC .... *A61M 5/31515* (2013.01); *A61M 5/31528* (2013.01); *A61M 2005/31521* (2013.01)

(58) Field of Classification Search
CPC .......... A61M 5/31578; A61M 5/31528; A61M 5/315; A61M 5/31515
See application file for complete search history.

(56) References Cited

U.S. PATENT DOCUMENTS

| 5,562,624 A | 10/1996 | Righi et al. |
| 2006/0184117 A1 | 8/2006 | Knight et al. |
| 2010/0280461 A1 | 11/2010 | Forstreuter |

(Continued)

FOREIGN PATENT DOCUMENTS

| CN | 101641126 A | 2/2010 |
| CN | 102639173 A | 8/2012 |

(Continued)

OTHER PUBLICATIONS

PCT Search Report for International Appliaction No. PCT/CN2018/104607, dated May 29, 2019, 9 pages.

*Primary Examiner* — Tiffany Legette
(74) *Attorney, Agent, or Firm* — Bradley J. Thorson; DeWitt LLP

(57) ABSTRACT

A plunging apparatus for a syringe is applied to connect with a driving assembly of an injection device and a medicine vial. The plunging apparatus has a pushing element connected with a connection element by a unidirectional check element. The rear end of the connection element is connected with a pushing rod. The front end of the pushing rod has an ejection element and a spring. A threaded collar is mounted around the pushing rod, and an injection rod is mounted in the pushing rod. The connection element is inserted into a rear opening of the medicine vial. Engagement hooks on the ejection element can be pressed by medicine vial. The spring forces the ejection element to move forward to push the pushing element to abut the piston. Accordingly, the medicine vial can be used immediately after being combined with the injection device without discharging air manually.

8 Claims, 13 Drawing Sheets

(56) References Cited

U.S. PATENT DOCUMENTS

2018/0050159 A1    2/2018  Enge et al.
2018/0078709 A1*   3/2018  Yeh ........................ A61M 5/24

FOREIGN PATENT DOCUMENTS

| CN | 105311714 A | 2/2016 |
|---|---|---|
| CN | 105879159 A | 8/2016 |
| CN | 106139325 A | 11/2016 |
| CN | 206372352 U | 8/2017 |
| CN | 107427643 A | 12/2017 |
| EP | 1759728 B1 | 11/2010 |
| EP | 3175875 A1 | 6/2017 |
| GB | 993309 A | 5/1965 |
| JP | 2012525172 A | 10/2012 |
| JP | 2016537105 A | 12/2016 |
| JP | 20180508311 A | 3/2018 |
| TW | 200940118 A | 10/2009 |
| TW | 201831212 A | 9/2018 |
| WO | 2006008086 A1 | 1/2006 |
| WO | 2015074982 A1 | 5/2015 |

\* cited by examiner

PLUNGING APPARATUS FOR SYRINGE

BACKGROUND OF THE INVENTION

1. Field of the Invention

The present invention relates to a syringe, and more particularly to a plunging apparatus for a syringe, wherein when the plunging apparatus is connected with a medication vial containing medicine inside, a pushing rod of a rotating driving mechanism can be moved automatically to a starting position where the pushing rod abuts against a piston in the medication vial.

2. Description of Related Art

For safety, an injection device can only be used for pre-determined times of shots. A conventional injection device includes two types, wherein one type is quantitative type and the other is time-metering type. In a conventional injection device of the quantitative type, after the injection device is connected with a medication vial, a pushing rod mounted on a rear end of the injection device is pushed. Consequently, a piston in the medication vial is pushed to move for a predetermined distance with the transmission of a driving assembly of the injection device. To make the conventional injection device operated laborsavingly, the driving assembly of the conventional injection device has a composition of a large screw travel and a small screw travel to transfer a straight force provided by a user pushing the pushing rod of the injection device to a rotation force. With the rotation force of the large screw travel being transferred to the pushing force for injection medicine provided by the small screw travel, a fixed amount of medication can be injected and the injection device is laborsaving in operation.

However, after the pushing device of the driving assembly of the conventional injection device is connected with the medicine vial, a spaced interval is formed between the pushing rod of the driving assembly and the piston of the medicine vial. Therefore, before injecting medicine into a person, the pushing rod of the driving assembly has to be moved to a position where the pushing rod abuts the piston in the medicine vial to discharge air in the spaced interval manually. Consequently, medicine is injected into a person by the injection device connected with the medicine vial. The action of discharging air manually causes inconvenience in operation of the conventional injection device, and the conventional injection device has to be improved.

SUMMARY OF THE INVENTION

The main objective of the invention is to provide a plunging apparatus for a syringe to solve the problem of inconvenience caused by that the user has to manually rotate the driving assembly to discharge the air.

To solve the problem, this invention provides a plunging apparatus for a syringe, disposed in a threaded driving mechanism of a syringe, and connected with a medication vial, characterized in that the plunging apparatus comprises: a pushing element comprising a threaded pushing member and a pushing board mounted on a front end of the threaded pushing member, and the pushing member having a thread formed on an outer surface of the pushing member and at least one channel defined in the outer surface of the threaded pushing member; a unidirectional check element mounted around the pushing element and comprising an annular body having
  an inner hole defined in the annular body, wherein the threaded pushing member extends into the inner hole of the annular body; and
  at least one rib formed on an inner surface of the inner hole and engaged respectively with the at least one channel in the threaded pushing member to allow the threaded pushing member to axially move forward and rearward relative to the unidirectional check element; and
at least one unidirectional ratchet resilient tab formed on an outer surface of the annular body;
a connection element mounted around the pushing element and the unidirectional check element and comprising
  a front end, wherein the pushing board of the pushing element is located outside the front end of the connection element;
a connection base having
  a unidirectional ratchet toothed recess defined in the connection base and having a front opening, wherein the unidirectional check element is mounted in the unidirectional ratchet toothed recess and the at least one unidirectional ratchet resilient tab is engaged with the unidirectional ratchet toothed recess;
  a connection board located at a rear end of the unidirectional ratchet toothed recess; and
  a threaded hole defined in the connection board, screwed with the threaded pushing member of the pushing element, and having a tooth width smaller than a pitch of the threaded pushing member of the pushing element to form a movement interval to allow the pushing element to axially move forward and rearward in a range of the movement interval; and
  at least one resilient hook formed on a rear end of the connection base;
a pushing rod connected with a rear end of the connection element and having
  a threaded segment having a pushing thread formed on an outer surface of the threaded segment and having a handedness same as a handedness of the thread on the threaded pushing member;
  a front segment formed on a front end of the threaded segment and having a front chamber provided with a front opening, a rear chamber provided with a rear opening, and an abutment board formed between the front chamber and the rear chamber; and
  at least one hole defined radially in an outer surface of the front segment and communicating with the front chamber, wherein the at least one resilient hook of the connection element is mounted around the front segment and corresponds respectively to the at least one hole in position;
an ejection element mounted in the front chamber of the pushing rod and comprising
  a base board;
  at least one engagement hook formed on a front side of the base board and engaged respectively with the at least one hole; and
  an ejection stub formed on the front side of the base board, corresponding to a rear end of the threaded pushing member in position, and having a front end spaced from the rear end of the threaded pushing member;
a spring mounted compressibly in the front chamber of the pushing rod and having two ends abutting respectively against the base board of the ejection element and the abutment board of the pushing rod;

a threaded collar threaded with the pushing rod and having a threaded hole screwed with the threaded segment of the pushing rod; and an injection rod mounted in the rear chamber of the pushing rod.

Wherein, the connection element includes two resilient hooks spaced at even angular intervals;

the pushing rod includes two holes defined in the front segment and corresponding respectively to the two resilient hooks in position; and the ejection element includes two engagement hooks engaged respectively with the two holes.

Wherein, the connection element has two engagement portions formed on a rear side of the connection base;

the two engagement portions and the two resilient hooks are arranged in an alternative manner;

each engagement portion has an engaging hole defined in the engagement portion; and the front segment of the pushing rod has two engaging blocks engaged respectively with the engaging holes in the two engagement portions of the connection element.

Wherein, the threaded pushing member includes two channels formed on the outer surface of the threaded pushing member and diametrically opposite each other; and the annular body of the unidirectional check element includes two ribs formed on the inner surface of the inner hole and engaged respectively with the two channels.

Wherein, the pushing rod has a rear segment formed on a rear end of the threaded segment and having at least one resilient block formed on the rear segment at a position adjacent to the threaded segment and at least one through hole formed respectively around the at least one resilient block; and each one of the at least one resilient block has a rear end connected with the rear segment and a free front end.

The advantages of the present invention are as follows. The plunging apparatus in accordance with the present invention can be applied to a driving assembly of an injection device and is connected with a medicine vial, the connection element is connected with the pushing element, and the unidirectional check element is inserted into a rear opening of the medicine vial. The inner periphery of the rear opening will press the resilient hooks of the connection element to bend inward. The bent resilient hooks will press engagement hooks of the ejection element to be bent inward and to disengage from the holes in the front segment of the pushing rod so as to unlock the ejection element. With the energy stored by the compressed spring, the ejection element is ejected to move forward and to push the pushing element to move forward a predetermined distance and to abut against the piston in the medicine vial. The medicine in the medicine vial is pressed by the forward moving piston, and the air in the front end of the medicine vial can be discharged completely via a needle. Accordingly, the medicine vial can be completely filled with medicine. After the injection device is combined with the medicine vial, the air can be discharged automatically but not manually. Therefore, the convenience of using the injection device can be improved.

Furthermore, with the engagement between the unidirectional ratchet resilient tab of the unidirectional check element and the unidirectional ratchet toothed recess in the connection element, the pushing element can be kept from moving backward to ensure that the pushing element of the plunging apparatus can abut against the piston in the medicine vial. Accordingly, the dose of the medicine can be controlled precisely.

| List of the referenced numerals | |
| --- | --- |
| 1 plunging apparatus | |
| 2 medicine vial | 2A piston |
| 2B rear opening | |
| 10 pushing element | 11 threaded pushing member |
| 110 thread | 111 front end |
| 112 rear end | 113 channel |
| 12 pushing board | 121 through hole |
| 20 unidirectional check element | 21 annular body |
| 210 inner hole | 211 rib |
| 22 unidirectional ratchet resilient tab | 221 unidirectional ratchet claw |
| 30 connection element | 31 connection base |
| 311 unidirectional ratchet toothed recess | 312 connection board |
| 313 threaded hole | 32 resilient hook |
| 33 engagement portion | 331 engaging hole |
| 40 pushing rod | 41 threaded segment |
| 42 front segment | 421 hole |
| 422 engaging block | 43 rear segment |
| 44 front chamber | 45 rear chamber |
| 46 abutment board | 47 resilient block |
| 48 through hole | |
| 50 ejection element | 51 base board |
| 52 engagement hook | 53 ejection stub |
| 54 positioning flange | |
| 60 spring | |
| 70 threaded collar | 71 threaded hole |
| 80 injection rod | 81 abutment end |

DETAILED DESCRIPTION OF PREFERRED EMBODIMENT

Other objects, advantages and novel features of the invention will become more apparent from the following detailed description when taken in conjunction with the accompanying drawings.

Figure 1:
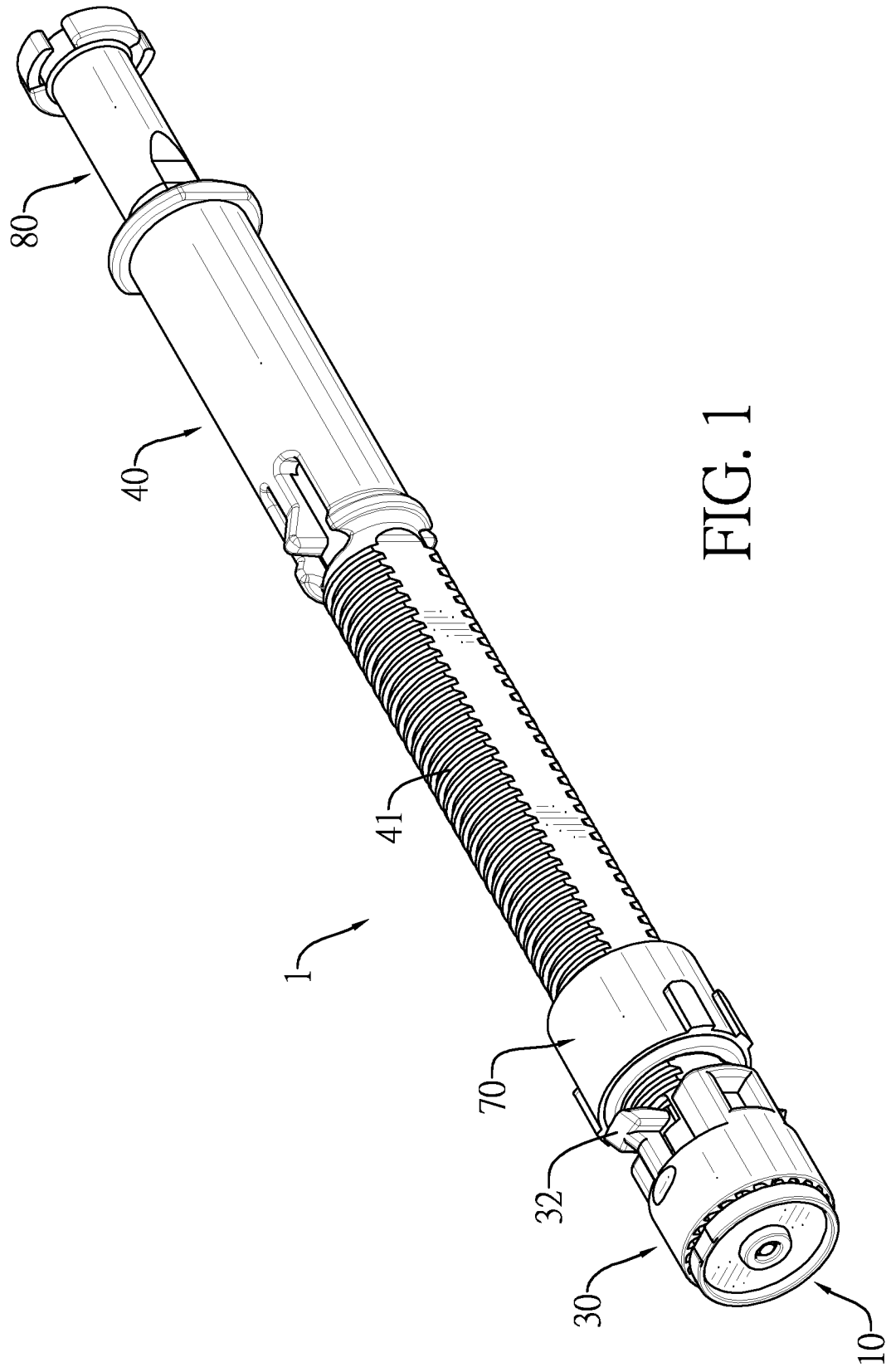
FIG. 1 is a perspective view of a preferred embodiment of a plunging apparatus for a syringe in accordance with the present invention.
Figure 2:
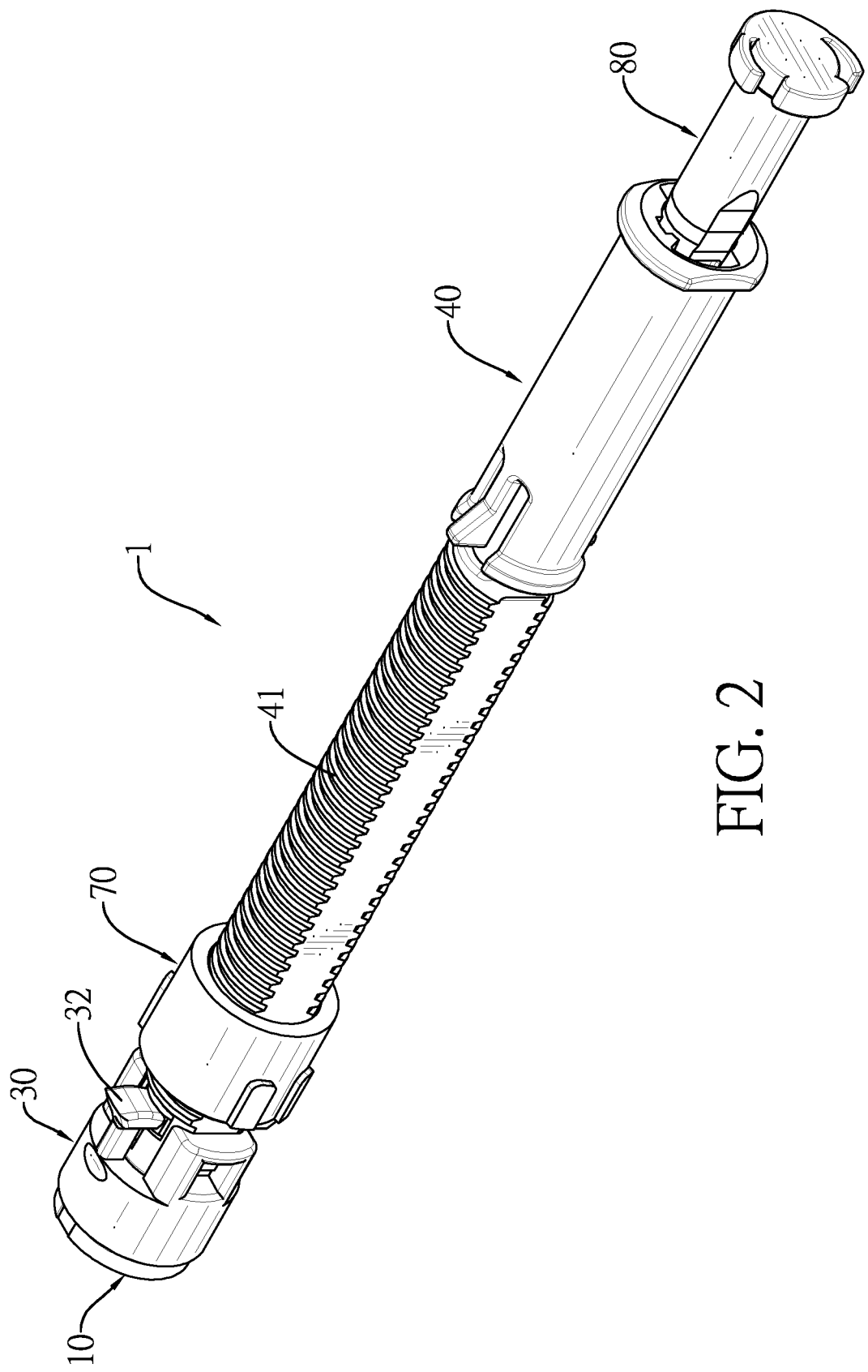
FIG. 2 is a perspective view of the plunging apparatus in FIG. 1.
Figure 3:
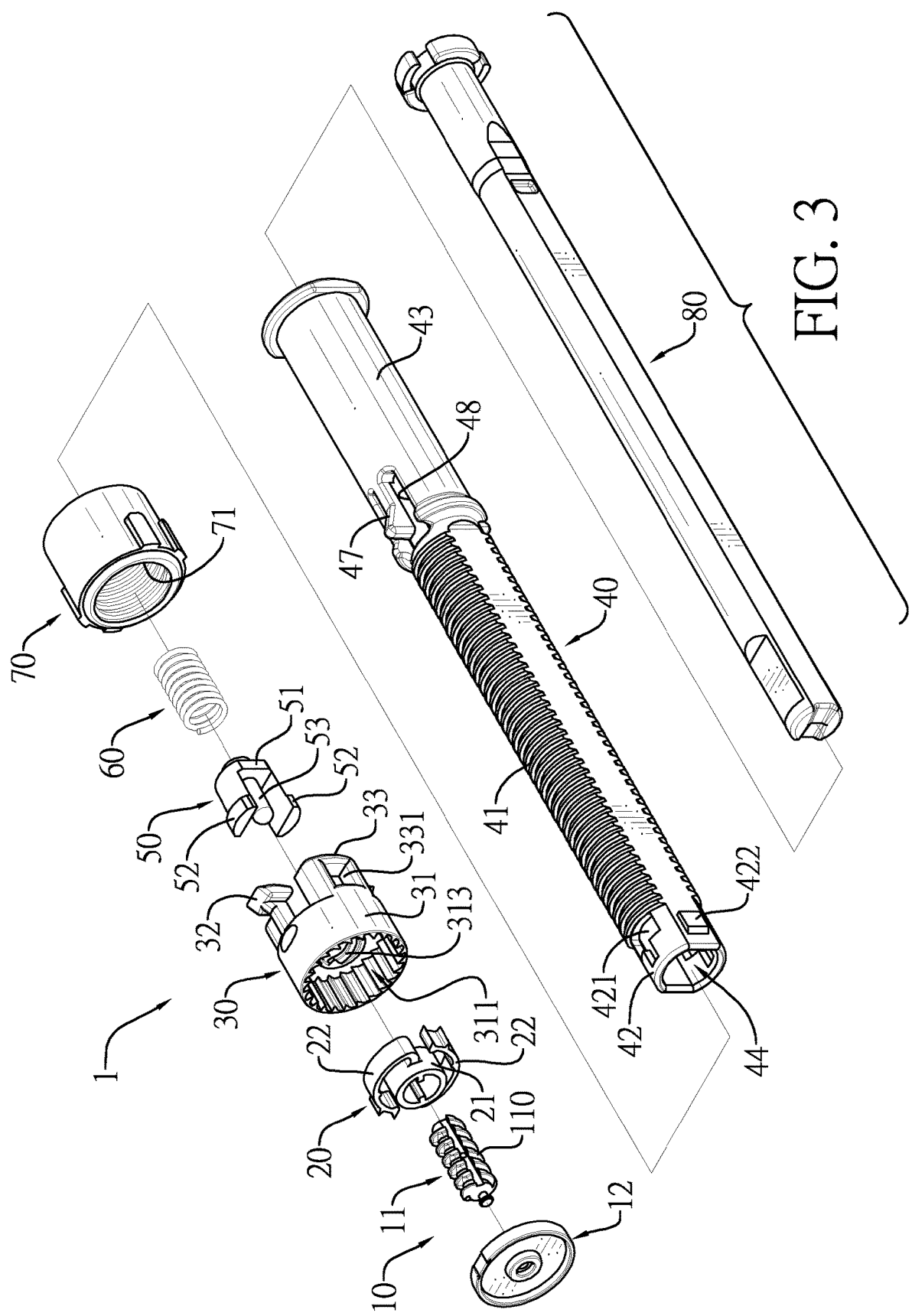
FIG. 3 is an exploded perspective view of the plunging apparatus in FIG. 1.
Figure 4:
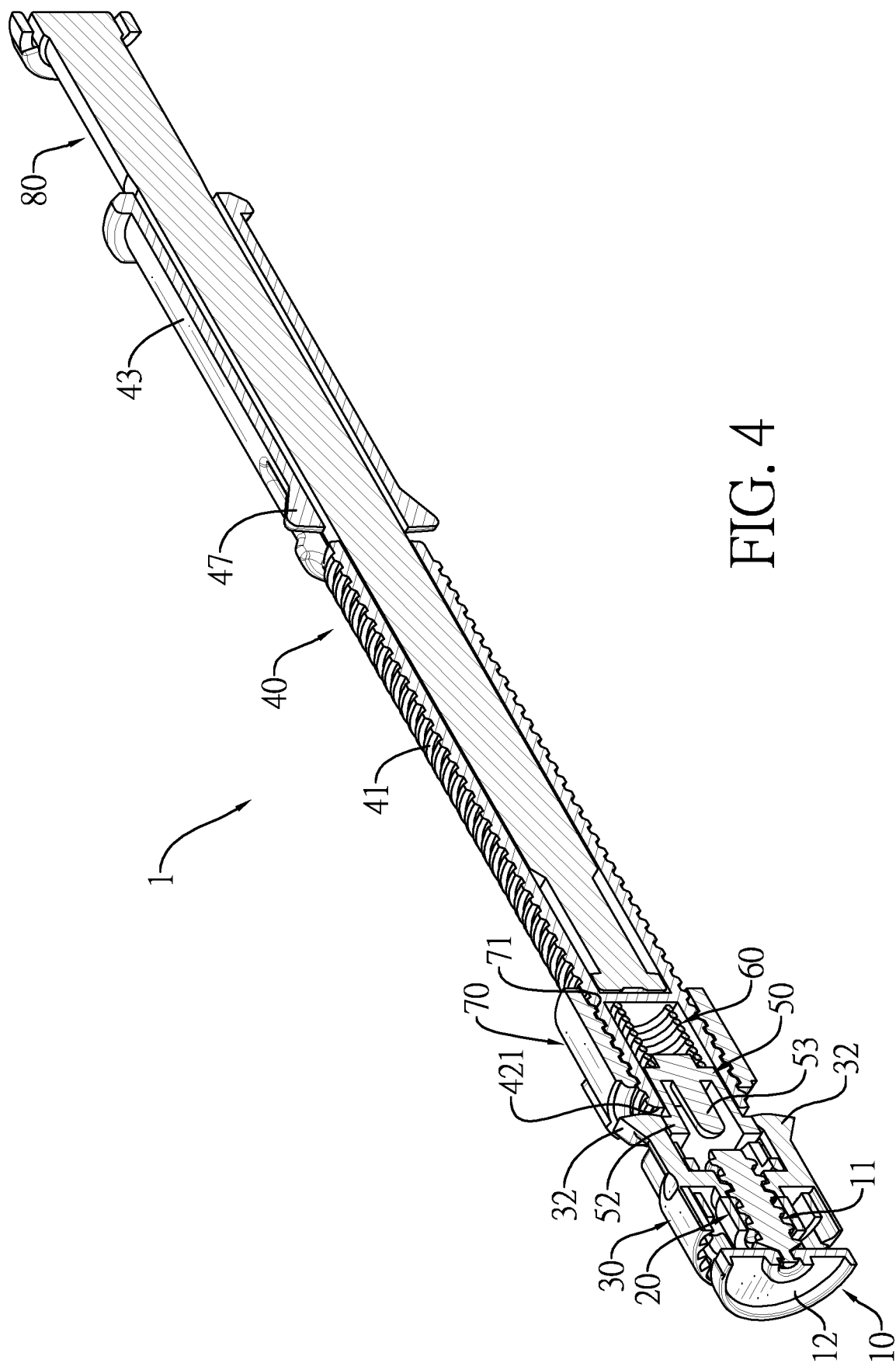
FIG. 4 is a cross sectional perspective view of the plunging apparatus in FIG. 1.
Figure 5:
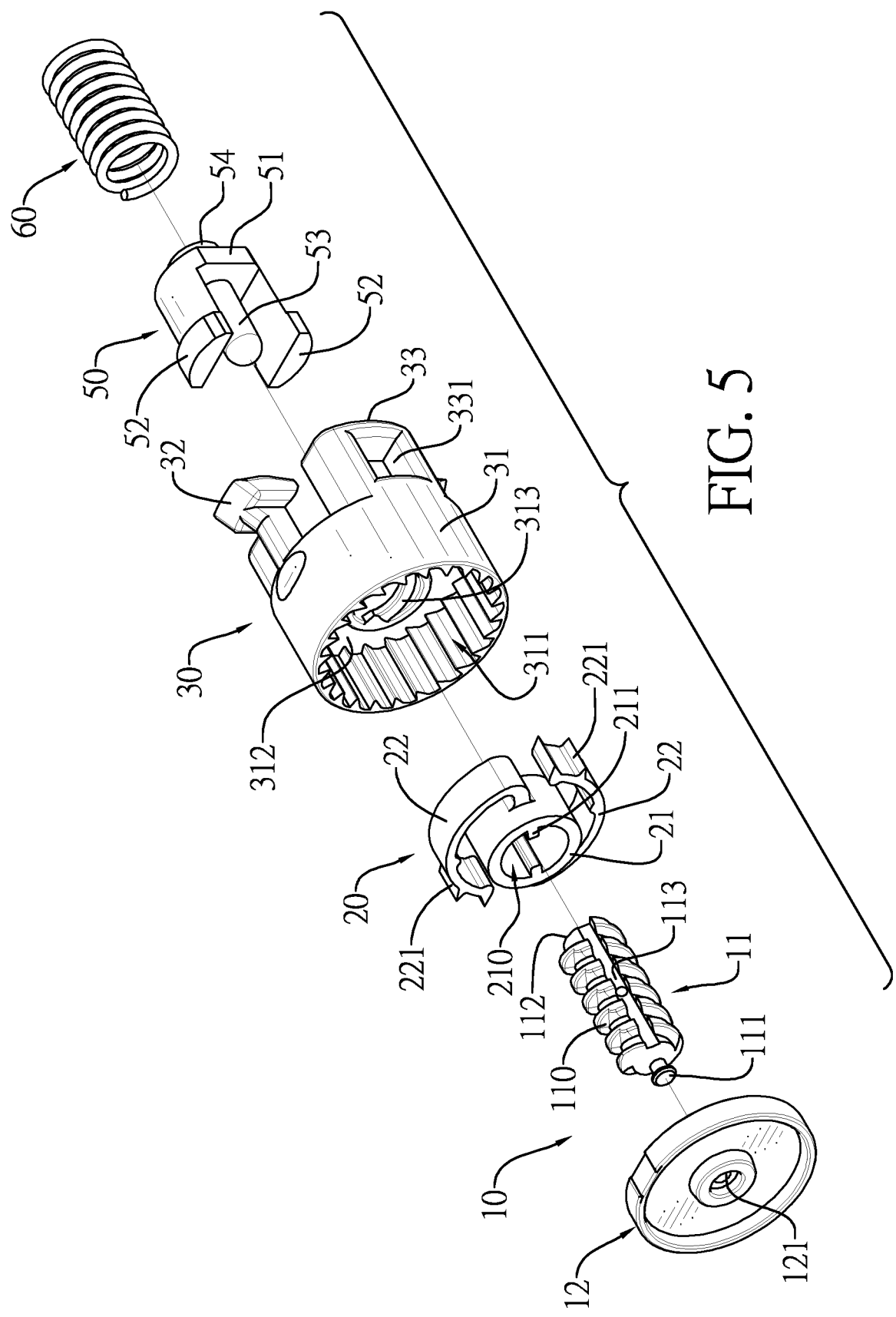
FIG. 5 is an exploded perspective view of parts of the plunging apparatus in FIGS. 1 to 3.
Figure 6:
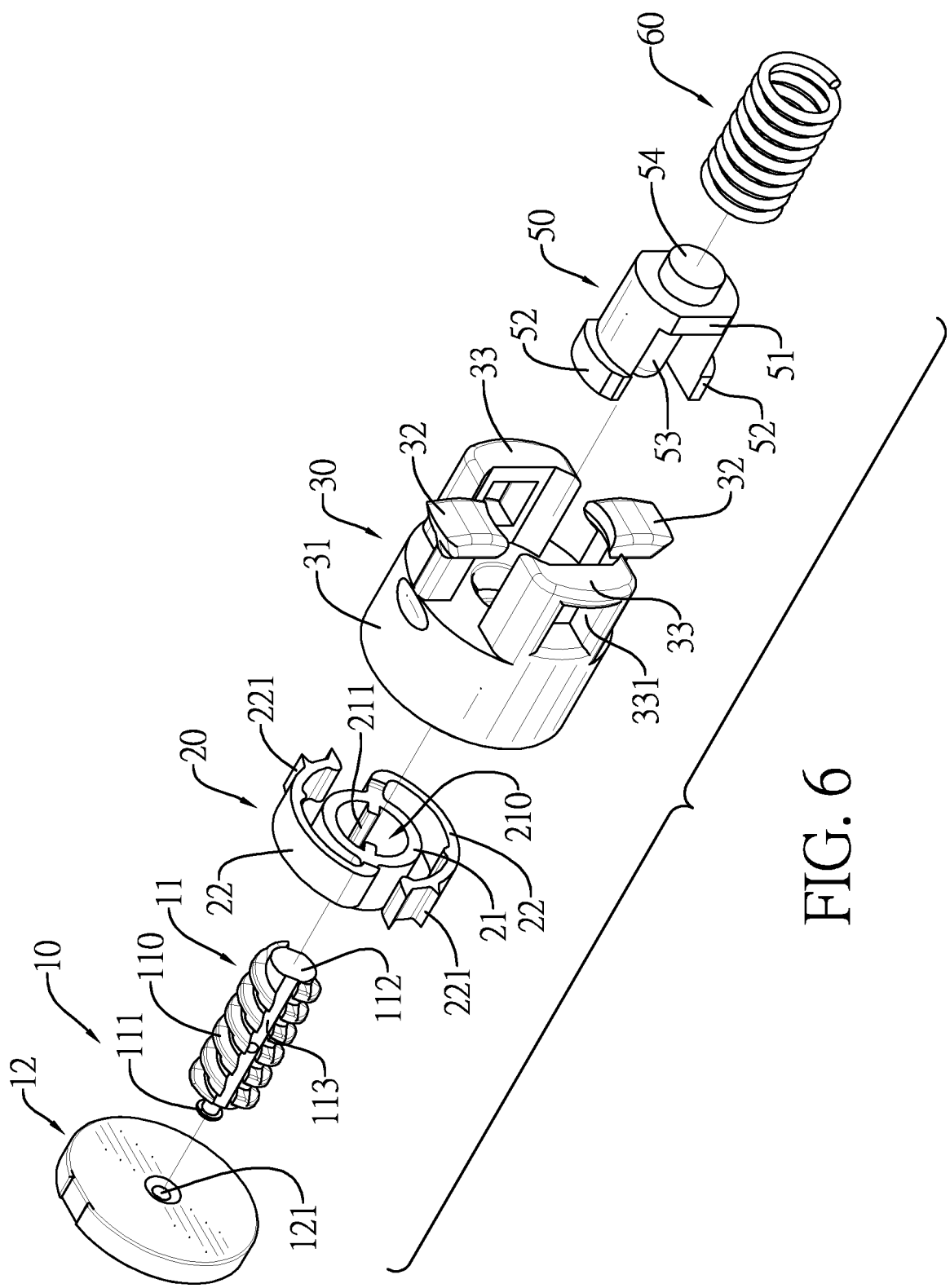
FIG. 6 is another exploded perspective view of the parts of the plunging apparatus in FIG. 5.
Figure 7:
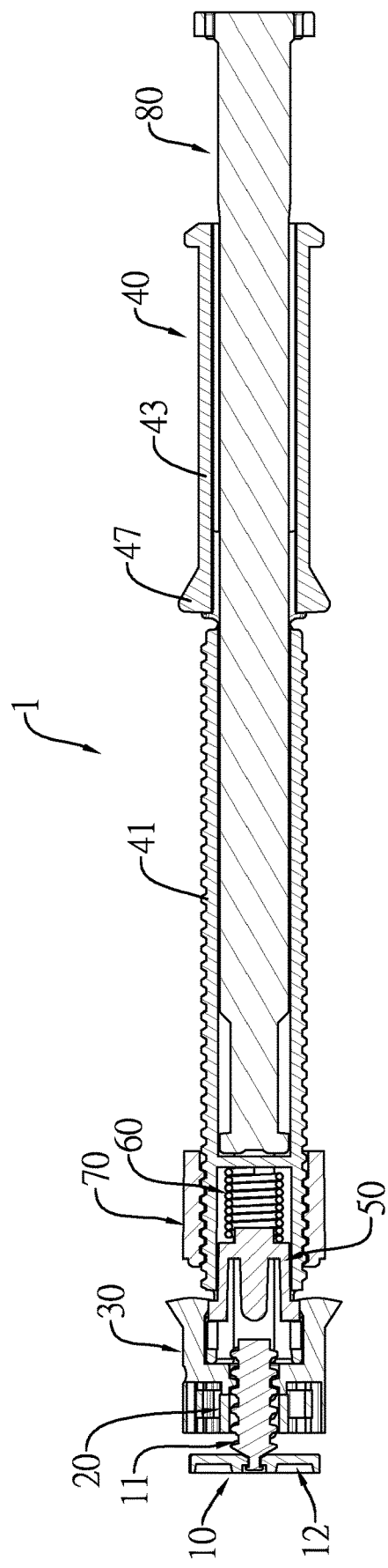
FIG. 7 is a cross sectional side view of the plunging apparatus in FIG. 1.
Figure 8:
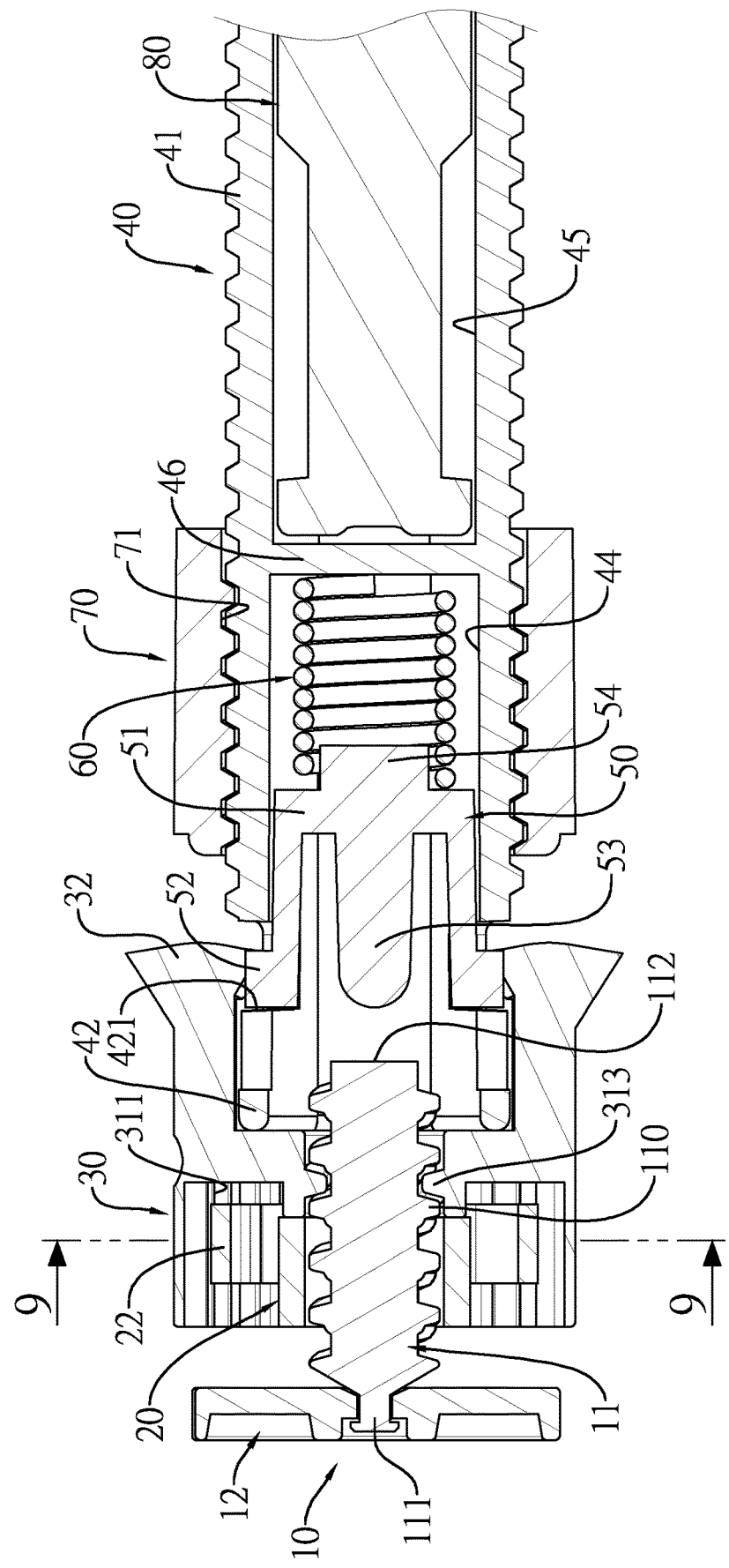
FIG. 8 is an enlarged cross sectional side view of the plunging apparatus in FIG. 7.

With reference to FIGS. 1 to 3, a preferred embodiment of a plunging apparatus 1 for a syringe in accordance with the present invention comprises a pushing element 10, a unidirectional check element 20, a connection element 30, a pushing rod 40, an ejection element 50, a spring 60, a threaded collar 70, and an injection rod.

With reference to FIGS. 1 to 3, the pushing element 10 comprises a threaded pushing member 11 and a pushing board 12. Two ends of the threaded pushing member 11 are defined respectively as a front end 111 and a rear end 112. A thread 110 is formed on an outer surface of the threaded pushing member 11 and is a right hand thread. At least one channel 113 is defined in the outer surface of the threaded pushing member 11. In the preferred embodiment, the threaded pushing member 11 includes two channels 113 defined in the outer surface and being diametrically opposite each other. The pushing board 12 is mounted on the front end 111 of the threaded pushing member 11. The pushing board 12 has a through hole 121 defined in a center thereof. The front end 111 of the threaded pushing member 11 extends into the through hole 121. With reference to FIG. 3, the threaded pushing member 11 and the pushing board 12 are individual components and are combined with each other. Alternatively, the threaded pushing member 11 and the pushing board 12 can be formed as a single piece (not shown).

With reference to FIGS. 3 to 8, the unidirectional check element 20 is mounted around the pushing element 10, and the pushing element 10 is axially moveable inside the unidirectional check element 20 and can rotate with the unidirectional check element 20. The unidirectional check element 20 comprises an annular body 21 and at least one unidirectional ratchet resilient tab 22. The annular body 21 has an inner hole 210, and at least one rib 211 is formed on and extends longitudinally on an inner surface of the inner hole 210. In the preferred embodiment, the inner hole 210 includes two ribs 211. The threaded pushing member 11 of the pushing element 10 is mounted in the inner hole 210 in the annular body 21, and the ribs 211 of the annular body 21 are engaged respectively with the channels 113 in the threaded pushing member 11. The at least one unidirectional ratchet resilient tab 22 is formed on an outer surface of the annular body 21. In the preferred embodiment, the unidirectional check element 20 includes two unidirectional ratchet resilient tabs 22, and each unidirectional ratchet resilient tab has a unidirectional ratchet claw 221.

Figure 9:
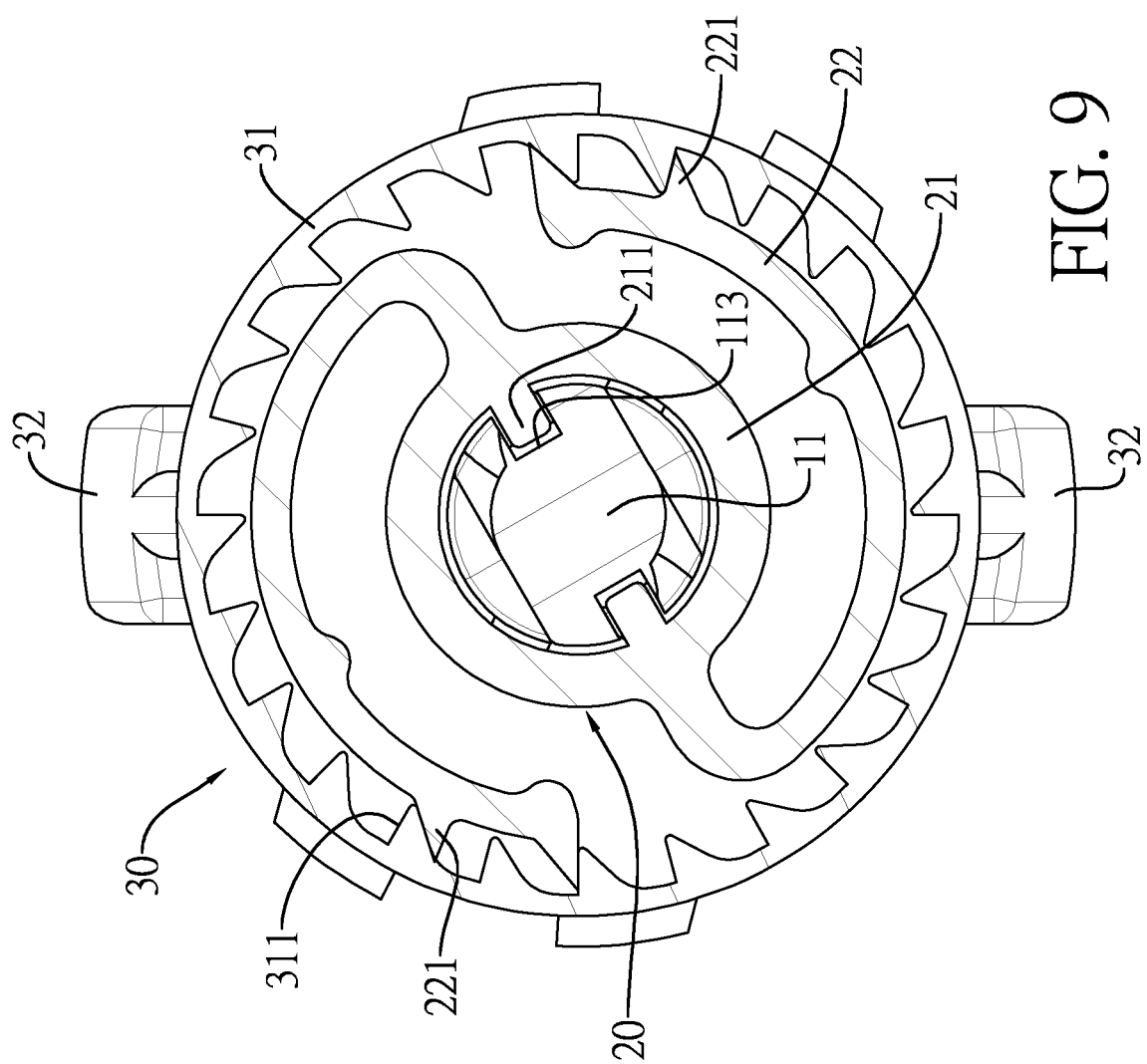
FIG. 9 is a cross sectional end view of the plunging apparatus along the line A-A in FIG. 8.
Figure 10:
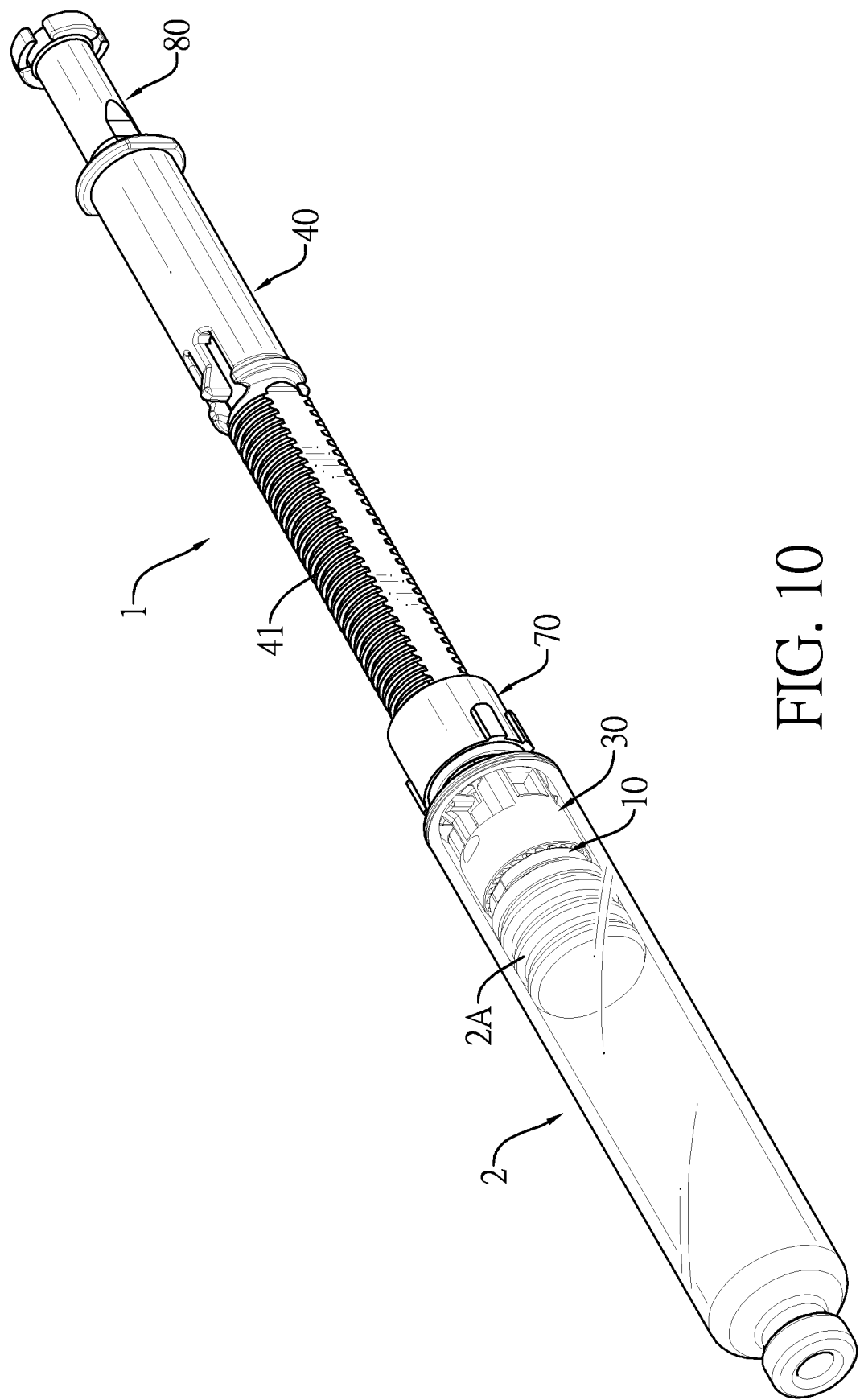
FIG. 10 is a perspective view of the plunging apparatus in FIG. 1 connected with a medicine vial.

With reference to FIGS. 3 to 8, the connection element 30 is mounted around the pushing element 10 and the unidirectional check element 20 and comprises a connection base 31 and at least one resilient hook 32. The connection base 31 has a unidirectional ratchet toothed recess 311 defined in the connection base 31 and having a front opening. A connection board is located at a rear end of the unidirectional ratchet toothed recess 311. The unidirectional ratchet toothed recess 311 has multiple single oblique ratchet teeth. A threaded hole 313 is defined in the connection board 312. The threaded hole 313 in the connection board 312 has a tooth width smaller than a pitch of the threaded pushing member 11 of the pushing element 10. The pushing board 12 of the pushing element 10 is located outside the front end of the connection element 30. With reference to FIG. 9, the unidirectional check element 20 is located inside the unidirectional ratchet toothed recess 311, and the at least one unidirectional ratchet resilient tab 22 of the unidirectional check element 20 is engaged with the unidirectional ratchet toothed recess 311. Accordingly, the unidirectional check element 20 can only unidirectionally rotate in the connection element 30. The threaded pushing member 11 of the pushing element 10 is screwed with the threaded hole 313 in the connection board 312. With the tooth width of the threaded hole 313 in the connection base 321 smaller than the pitch of the threaded pushing member 11 of the pushing element 10, a movement interval is formed therebetween to allow the pushing element 10 to axially move forward and rearward in a range of the movement interval. The at least one resilient hook 32 is formed on a rear end of the connection base 31 and is bendable and resilient. In the preferred embodiment, the connection element 30 includes two resilient hooks 32 spaced at even angular intervals. The connection element 30 has two engagement portions 33 formed on a rear side of the connection base 31, and each engagement portion 33 has an engaging hole 331 defined in the engagement portion 33. The two engagement portions 33 and the two resilient hooks 32 are arranged in an alternative manner.

With reference to FIGS. 3 to 8, the pushing rod 40 is connected with the rear end of the connection element 30 and comprises a threaded segment 41, a front segment 42, and a rear segment 43. A pushing thread is formed on an outer surface of the threaded segment 41 and is a right hand thread. The pushing thread of the threaded segment 41 and the thread on the threaded pushing member 11 of the pushing element 11 have a same handedness. The front segment 42 is formed on a front end of the threaded segment 41, and the rear segment 43 is formed on a rear end of the threaded segment 41. A front chamber 44 provided with a front opening is formed in the front end of the pushing rod 40. A rear chamber 44 is defined in the pushing rod 40 at a position behind the front chamber 45 provided with a rear opening. An abutment board 46 is formed between the front chamber 44 and the rear chamber 45.

With reference to FIGS. 3 to 8, in the preferred embodiment, the abutment board 46 of the pushing rod 40 is located inside the threaded segment 41 in a position being adjacent to the front end of the front segment 42. The front chamber 44 extends from the front end of the pushing rod 40 to the front end of the threaded segment 41 through the front segment 42. At least one hole 421 is defined radially in an outer surface of the front segment 42 and communicates with the front chamber 44. In the preferred embodiment, the front segment 42 has two holes 421, and two engaging blocks 422 are formed on an outer surface of the front segment 42. The two engaging blocks 422 on the front segment 42 of the pushing rod 40 are engaged respectively with the engaging holes 331 in the two engagement portions 33 of the connection element 30. The resilient hooks 32 correspond respectively to the holes 421 in the pushing rod 40 in position.

With reference to FIGS. 3 to 8, in the preferred embodiment, the rear chamber 45 extends from the threaded segment 41 to the rear end of the pushing rod 40 through the rear segment 43. At least one resilient block 47 is formed on the rear segment 43 at a position adjacent to the threaded segment 41, and at least one through hole 48 is formed respectively around the at least one resilient block 47. Each engaging block 47 has a rear end connected with the rear segment 43 and a free front end.

With reference to FIGS. 3 to 8, the ejection element 50 is mounted in the front chamber 44 of the pushing rod 40 and comprises a base board 51, at least one engagement hook 52, and an ejection stub 53. The at least one engagement hook 52 and the ejection stub 53 are formed on and extend forward from a front side of the base board 51. In the preferred embodiment, the ejection element 50 includes two engagement hooks 52. In an original position, the engagement hooks 52 are engaged respectively with the holes 421 in the pushing rod 40, such that the ejection element 50 is locked in the pushing rod 40. The ejection stub 53 is located in a central portion of the base board 51 and corresponds to the rear end 112 of the threaded pushing member 11. In the original positon, the front end of the ejection stub 53 is spaced from the rear end 112 of the threaded pushing member 12 at a spaced interval. In the preferred embodiment, a positioning flange 54 is formed on a rear side of the base board 51.

With reference to FIGS. 3 to 8, the spring 60 is mounted compressibly in the front chamber 44 of the pushing rod 40 and has two ends abutting respectively against the base board 51 of the ejection element 50 and the abutment board 46 of the pushing rod 40. In the original position where the ejection element 50 is locked inside the front chamber 44 of the pushing rod 40, the spring 60 is compressed to store energy. In the preferred embodiment, the front end of the spring 60 is mounted around the positioning flange 54 on the rear side of the base board 51 of the ejection element 50.

With reference to FIGS. 3 to 4 and 7 to 8, the threaded collar 70 is screwed with the pushing rod 40 and has a threaded hole 71 screwed with the threaded segment 41 of the pushing rod 40.

With reference to FIGS. 3 to 4 and 7 to 8, the injection rod 80 is mounted in the rear chamber 45 of the pushing rod 40 and has a front end facing the abutment board 46 of the pushing rod 40.

With reference to FIGS. 10 to 13, when the plunging apparatus 1 in accordance with the present invention is in use and is connected with a quantitative type injection device, the plunging apparatus 1 is mounted in a driving assembly of the injection device. The driving assembly comprises a screw tube, a screw sleeve, and a threaded driving rod. The driving assembly may be a conventional one, and the screw tube, the screw sleeve, and the threaded driving rod are not components of this invention. Thus, the detailed structure of the driving assembly is omitted. The screw tube of the driving assembly is mounted in the screw sleeve, and the threaded driving rod is mounted in the screw tube and the screw sleeve and has a function of movement driven by a large screw travel. The plunging apparatus 1 is mounted in the driving assembly, and the threaded collar 70 is mounted in the screw tube and can be driven to rotate in a fixed position. The threaded collar 70 and the pushing rod 40 have a screwing structure of a small screw travel, such that the rotation force provided by the large screw travel can be transferred to a medicine-pushing force provided by the small screw travel. The injection rod 80 of the plunging apparatus 1 protrudes out from an end cap connected with a rear end of the driving assembly, and a user can push the end cap.

Figure 11:
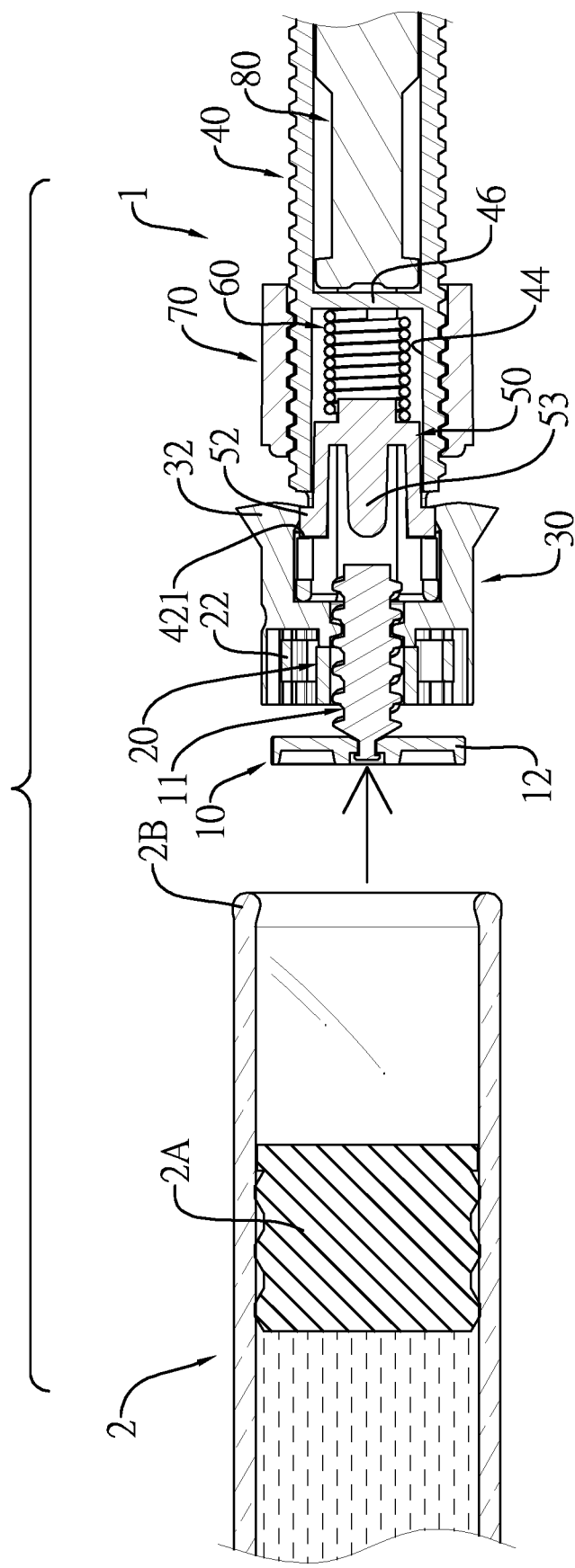
FIG. 11 is a first operational cross sectional side view of the plunging apparatus in FIG. 1.
Figure 12:
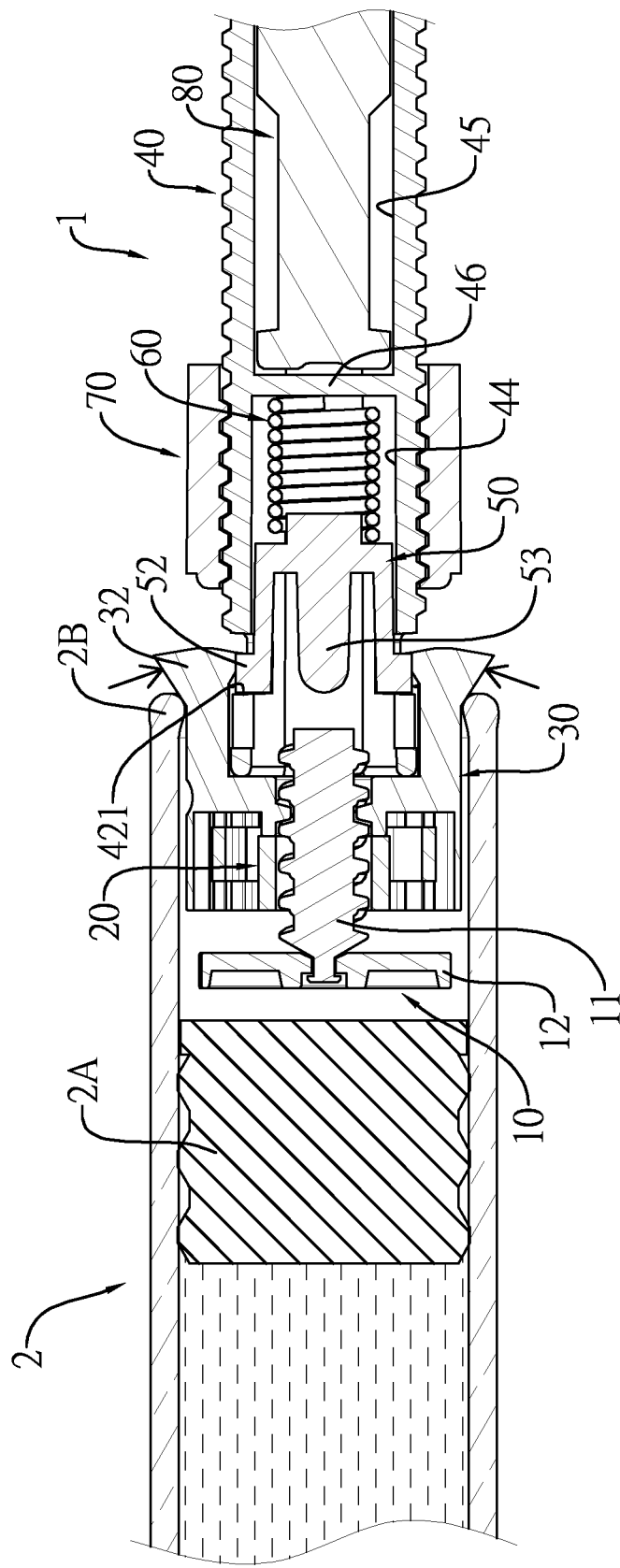
FIG. 12 is a second operational cross sectional side view of the plunging apparatus in FIG. 1.
Figure 13:
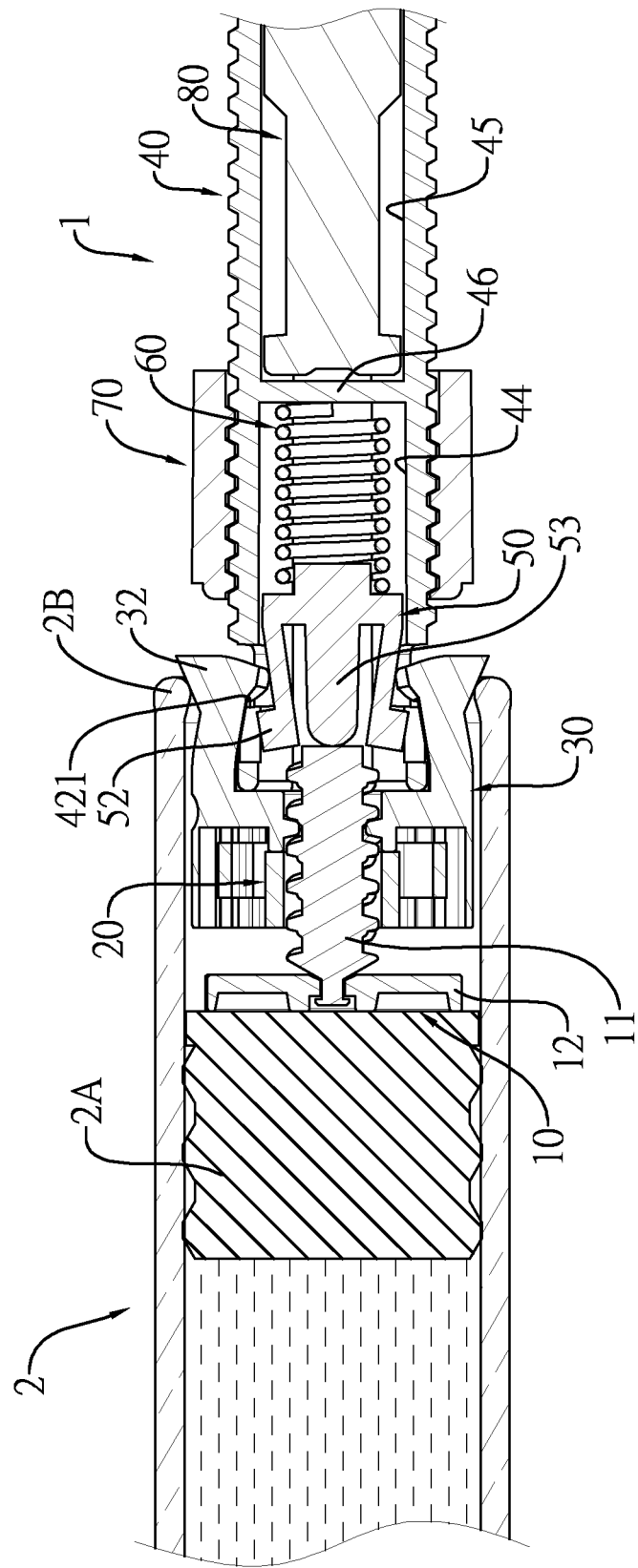
FIG. 13 is a third operational cross sectional side view of the plunging apparatus in FIG. 1.

With reference to FIGS. 11 to 13, when the plunging apparatus 1 is in operation and is connected with a medicine vial 2, the connection element 30 connected with the pushing element 10 and the unidirectional check element 20 is inserted into a rear opening of the medicine vial 2. The inner periphery of the rear opening 2B will press the resilient hooks 32 of the connection element 30 to bend inward and the bent resilient hooks 32 will press engagement hooks 52 of the ejection element 50 to be bent inward and to disengage from the holes 421 in the front segment 42 of the pushing rod 40. Thus, the ejection element 50 is unlocked. The energy stored by the compressed spring 60 will provide a resilient force to eject the ejection element 50 to move forward, and the ejected ejection element 50 will push the pushing element 10 to move forward and to abut against the piston 2A in the medicine vial 2. Accordingly, the medicine inside the medicine vial 2 can be immediately injected into a person without discharging the air by manually pushing the driving assembly to push the pushing element to abut against the piston. Thus, the injection device is convenient in use. When the injection device is applied to inject medicine, the injection way of the injection device is same as that of a conventional one. With the small screw travel between the threaded collar 70 and the pushing rod 40, the driving assembly of the injection device can transfer a rotation force provided by a laborsaving large screw travel to a medicine-pushing force provided by a small screw travel. With the pushing rod pushing the connection element 30 and the pushing element 10 to move forward and to further push the medicine in the medicine vial 2 to be injected into a person, the forward moving pushing rod 40 can provide a forward pushing force to the pushing element 10 via the connection element 30, and the rear end of the threaded pushing member 11 of the pushing element is provided with the resilient force by the spring 60 and applied to the ejection element 50. With the engagement between the unidirectional ratchet resilient tab 22 of the unidirectional check element 20 and the unidirectional ratchet toothed recess 311 in the connection element 30, the pushing element 10 can be kept from moving backward to ensure that the pushing element 10 of the plunging apparatus can abut against the piston 2A in the medicine vial 2. Accordingly, the dose of the medicine can be controlled precisely.

As aforementioned, the plunging apparatus in accordance with the present invention can be applied to a driving assembly of an injection device and is connected with a medicine vial, the connection element connected with the pushing element, and the unidirectional check element is inserted into a rear opening of the medicine vial. The inner periphery of the rear opening will press the resilient hooks of the connection element to bend inward. The bent resilient hooks will press engagement hooks of the ejection element to be bent inward and to disengage from the holes in the front segment of the pushing rod so as to unlock the ejection element. With the energy stored by the compressed spring, the ejection element is ejected to move forward and to push the pushing element to move forward a predetermined distance and to abut against the piston in the medicine vial. The medicine in the medicine vial is pressed by the forward moving piston, and the air in the front end of the medicine vial can be discharged completely via a needle. Accordingly, the medicine vial can be completely filled with medicine. After the injection device is combined with the medicine vial, the air can be discharged automatically but not manually. Therefore, the convenience of using the injection device can be improved.

Furthermore, with the engagement between the unidirectional ratchet resilient tab of the unidirectional check element and the unidirectional ratchet toothed recess in the connection element, the pushing element can be kept from moving backward to ensure that the pushing element of the plunging apparatus can abut against the piston in the medicine vial. Accordingly, the dose of the medicine can be controlled precisely.

Even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A plunging apparatus for a syringe, disposed in a threaded driving mechanism of the syringe, and connected with a medication vial, characterized in that the plunging apparatus comprises:
- a pushing element comprising a threaded pushing member and a pushing board mounted on a front end of the threaded pushing member, and the threaded pushing member having a thread formed on an outer surface of the threaded pushing member and at least one channel defined in the outer surface of the threaded pushing member;
- a unidirectional check element mounted around the pushing element and comprising
  - an annular body having
    - an inner hole defined in the annular body, wherein the threaded pushing member extends into the inner hole of the annular body; and
    - at least one rib formed on an inner surface of the inner hole and engaged respectively with the at least one channel in the threaded pushing member to allow the threaded pushing member to axially move forward and rearward relative to the unidirectional check element; and
  - at least one unidirectional ratchet resilient tab formed on an outer surface of the annular body;
- a connection element mounted around the pushing element and the unidirectional check element and comprising
  - a front end, wherein the pushing board of the pushing element is located outside the front end of the connection element;
  - a connection base having
    - a unidirectional ratchet toothed recess defined in the connection base and having a front opening, wherein the unidirectional check element is mounted in the unidirectional ratchet toothed recess and the at least one unidirectional ratchet resilient tab is engaged with the unidirectional ratchet toothed recess;
    - a connection board located at a rear end of the unidirectional ratchet toothed recess; and
    - a threaded hole defined in the connection board, threaded with the threaded pushing member of the pushing element and having a tooth width smaller than a pitch of the threaded pushing member of the pushing element to form a movement interval to allow the pushing element to axially move forward and rearward in a range of the movement interval; and
  - at least one resilient hook formed on a rear end of the connection base;
- a pushing rod connected with a rear end of the connection element and having
  - a threaded segment having a pushing thread formed on an outer surface of the threaded segment and having a handedness same as a handedness of the thread on the threaded pushing member;
  - a front segment formed on a front end of the threaded segment and having a front chamber provided with a front opening, a rear chamber provided with a rear opening, and an abutment board formed between the front chamber and the rear chamber; and
  - at least one hole defined radially in an outer surface of the front segment and communicating with the front chamber, wherein the at least one resilient hook of the connection element is mounted around the front segment and corresponds respectively to the at least one hole in position;
- an ejection element mounted in the front chamber of the pushing rod and comprising
  - a base board;
  - at least one engagement hook formed on a front side of the base board and engaged respectively with the at least one hole; and
  - an ejection stub formed on the front side of the base board, corresponding to a rear end of the threaded pushing member in position, and having a front end spaced from the rear end of the threaded pushing member;
- a spring mounted compressibly in the front chamber of the pushing rod and having two ends abutting respectively against the base board of the ejection element and the abutment board of the pushing rod;
- a threaded collar screwed with the pushing rod and having a threaded hole threaded with the threaded segment of the pushing rod; and
- an injection rod mounted in the rear chamber of the pushing rod.

2. The plunging apparatus as claimed claim 1, wherein the pushing rod has a rear segment formed on a rear end of the threaded segment and having at least one resilient block formed on the rear segment at a position adjacent to the threaded segment and at least one through hole formed respectively around the at least one resilient block; and the at least one resilient block has a rear end connected with the rear segment and a free front end.

3. The plunging apparatus as claimed in claim 1, wherein the connection element includes two resilient hooks spaced at even angular intervals;
- the pushing rod includes two holes defined in the front segment and corresponding respectively to the two resilient hooks in position; and
- the ejection element includes two engagement hooks engaged respectively with the two holes.

4. The plunging apparatus as claimed in claim 3, wherein the pushing rod has a rear segment formed on a rear end of the threaded segment and having at least one resilient block formed on the rear segment at a position adjacent to the threaded segment and at least one through hole formed respectively around the at least one resilient block; and the at least one resilient block has a rear end connected with the rear segment and a free front end.

5. The plunging apparatus as claimed in claim 3, wherein the connection element has two engagement portions formed on a rear side of the connection base;
- the two engagement portions and the two resilient hooks are arranged in an alternative manner;
- each engagement portion has an engaging hole defined in the engagement portion; and
- the front segment of the pushing rod has two engaging blocks engaged respectively with the engaging holes in the two engagement portions of the connection element.

6. The plunging apparatus as claimed in claim 5, wherein the pushing rod has a rear segment formed on a rear end of the threaded segment and having at least one resilient block formed on the rear segment at a position adjacent to the threaded segment and at least one through hole formed respectively around the at least one resilient block; and the at least one resilient block has a rear end connected with the rear segment and a free front end.

7. The plunging apparatus as claimed in claim 5, wherein the threaded pushing member includes two channels formed on the outer surface of the threaded pushing member and diametrically opposite each other; and the annular body of the unidirectional check element includes two ribs formed on the inner surface of the inner hole and engaged respectively with the two channels.

8. The plunging apparatus as claimed in claim 7, wherein the pushing rod has a rear segment formed on a rear end of the threaded segment and having at least one resilient block formed on the rear segment at a position adjacent to the threaded segment and at least one through hole formed respectively around the at least one resilient block; and the at least one resilient block has a rear end connected with the rear segment and a free front end.

\* \* \* \* \*